(12) United States Patent
Meldrum et al.

(10) Patent No.: US 12,329,382 B2
(45) Date of Patent: Jun. 17, 2025

(54) THIXOTROPIC BIOCOMPATIBLE GEL FOR LIVE CELL OBSERVATION IN CELL COMPUTED TOMOGRAPHY

(71) Applicant: Arizona Board of Regents on behalf of Arizona State University, Scottsdale, AZ (US)

(72) Inventors: Deirdre Meldrum, Phoenix, AZ (US); Fengyu Su, Tempe, AZ (US); Laimonas Kelbauskas, Gilbert, AZ (US); Vivek Nandakumar, Tempe, AZ (US); Yanqing Tian, Tempe, AZ (US); Roger Johnson, Charleston, SC (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1392 days.

(21) Appl. No.: 16/631,040

(22) PCT Filed: Aug. 29, 2018

(86) PCT No.: PCT/US2018/048587
§ 371 (c)(1),
(2) Date: Jan. 14, 2020

(87) PCT Pub. No.: WO2019/046452
PCT Pub. Date: Mar. 7, 2019

(65) Prior Publication Data
US 2020/0178967 A1 Jun. 11, 2020

Related U.S. Application Data

(60) Provisional application No. 62/553,622, filed on Sep. 1, 2017.

(51) Int. Cl.
| | |
|---|---|
| A61B 17/11 | (2006.01) |
| A61B 5/00 | (2006.01) |
| C08J 3/075 | (2006.01) |
| C08K 3/36 | (2006.01) |
| C12N 11/02 | (2006.01) |
| G01N 1/30 | (2006.01) |
| G01N 15/1433 | (2024.01) |

(52) U.S. Cl.
CPC ............ *A61B 17/11* (2013.01); *A61B 5/0066* (2013.01); *C08J 3/075* (2013.01); *C08K 3/36* (2013.01); *C12N 11/02* (2013.01); *G01N 1/30* (2013.01); *G01N 15/1433* (2024.01); *C08J 2371/00* (2013.01)

(58) Field of Classification Search
CPC .... C08J 2371/00; C08J 2371/02; C08J 3/075; C08K 3/36; A61B 17/11; A61B 5/0066; C12N 11/02; G01N 1/28; G01N 1/30; G01N 15/1433
See application file for complete search history.

(56) References Cited

U.S. PATENT DOCUMENTS

| | | | |
|---|---|---|---|
| 4,788,052 A | 11/1988 | Ng | |
| 9,597,026 B2 | 3/2017 | Meldrum | |
| 10,022,718 B2 | 7/2018 | Martineau | |
| 10,162,162 B2 | 12/2018 | Wang | |
| 10,221,443 B2 | 3/2019 | Meldrum | |
| 10,391,485 B2 | 8/2019 | Meldrum | |
| 10,471,426 B2 | 11/2019 | Martineau | |
| 2009/0305412 A1 | 12/2009 | Ying | |
| 2011/0182995 A1* | 7/2011 | Asgary | .......... A61P 29/00 424/85.4 |
| 2012/0231533 A1 | 9/2012 | Holl | |
| 2012/0301913 A1 | 11/2012 | Youngbull | |
| 2013/0045182 A1 | 2/2013 | Gong | |
| 2013/0231359 A1 | 9/2013 | Chong | |
| 2015/0366974 A1 | 12/2015 | Holzer | |
| 2016/0202247 A1 | 7/2016 | Tian | |
| 2016/0215254 A1 | 7/2016 | Meldrum | |

(Continued)

FOREIGN PATENT DOCUMENTS

| | | |
|---|---|---|
| WO | 2010022391 A2 | 2/2010 |
| WO | 2010022391 A9 | 2/2010 |

(Continued)

OTHER PUBLICATIONS

Anis, Y., et al. "Diaphragm pico-liter pump for single-cell manipulation." Biomed Microdevices (2011) 13: 651. doi:10.1007/s10544-011-9535-5.
Avnir, D. et al., "Recent bio-applications of sol-gel materials", Journal of Materials Chemistry, 2006 [available online Nov. 2005], vol. 16, No. 11, pp. 1013-1030 DOI:10.1039/B512706H.
Baca, H. et al., "Cell-Directed Assembly of Lipid-Silica Nanostructures Providing Extended Cell Viability", Science, Jul. 2006, vol. 313, No. 5785, pp. 337-341 DOI:10.1126/science.1126590.
International Searching Authority. International Search Report and Written Opinion for application PCT/US2018/048587. Mailed on Dec. 18, 2018.
Kelbauskas, L. et al., "Platform for combined analysis of functional and biomolecular phenotypes of the same cell," Scientific Reports, vol. 7, article No. 44636, Mar. 16, 2017.

(Continued)

*Primary Examiner* — Ana L. Woodward
(74) *Attorney, Agent, or Firm* — Quarles & Brady, LLP; Yakov S. Sidorin

(57) ABSTRACT

A thixotropic and biocompatible gel, formed by combining of 4-arm polyethylene glycol with fumed silica (PEG-silica). The thixotropicity of the gel is affected by the ratio of PEG to silica. To study the gel's biocompatibility, the cell suspension in PBS or another medium was added to the PEG-silica gel via mixing to uniformly disperse the cells in the gel and then placed in an incubator before performing fluorescence live-dead assays. Duration of cell viability (cell life time) in gels was measured to be up to several days, depending on gel composition. Due to their optical and fluidic properties the gels are compatible with live cell imaging including 3D computed tomography and offer a means for moving the cells in a highly controllable manner by applying and removing pressure on the gels.

6 Claims, 7 Drawing Sheets

(56) References Cited

U.S. PATENT DOCUMENTS

| | | |
|---|---|---|
| 2018/0264468 A1 | 9/2018 | Anderson |
| 2018/0334700 A1 | 11/2018 | Messner |
| 2019/0126275 A1 | 5/2019 | Kelbauskas |
| 2019/0346361 A1 | 11/2019 | Meldrum |
| 2020/0047182 A1 | 2/2020 | Meldrum |
| 2020/0049694 A1 | 2/2020 | Anderson |
| 2020/0058140 A1 | 2/2020 | Meldrum |
| 2020/0063197 A1 | 2/2020 | Meldrum |
| 2020/0406253 A1 | 12/2020 | Meldrum |

FOREIGN PATENT DOCUMENTS

| | | |
|---|---|---|
| WO | 2010042478 A2 | 4/2010 |
| WO | 2010062654 A2 | 6/2010 |
| WO | 2015048009 A1 | 4/2015 |
| WO | 2017049122 A1 | 3/2017 |
| WO | 2017059220 A1 | 4/2017 |
| WO | 2017062807 A1 | 4/2017 |
| WO | 2017083817 A1 | 5/2017 |
| WO | 2017087473 A1 | 5/2017 |
| WO | 2017151978 A1 | 9/2017 |
| WO | 2017184998 A1 | 10/2017 |
| WO | 2018157064 A1 | 8/2018 |
| WO | 2018160998 A1 | 9/2018 |
| WO | 2018213269 A1 | 11/2018 |

OTHER PUBLICATIONS

Merza SA, et al. Microfluidic Device for Transport and Observation of Single Cells. ASME. ASME International Mechanical Engineering Congress and Exposition, vol. 9: Heat Transfer, Fluid Flows, and Thermal Systems, Parts A, B and C:2213-2220. doi:10.1115/IMECE2009-13019.

Mohsen-Sia, M. et al., "Measurement and Modeling of Density, Kinematic Viscosity, and Refractive Index for Poly (ethylene Glycol) Aqueous Solution at Different Temperatures", Journal of Chemical & Engineering Data, Aug. 2005, vol. 50, No. 5, pp. 1662-1666 DOI:10.1021/je050130t.

Nandakumar, V. et al. "Isotropic 3D nuclear morphometry of normal, fibrocystic and malignant breast epithelial cells reveals new structural alterations"; PLoS One 2012, 7, e0029230, doi:10.1371/journal.pone.0029230.

Nandakumar, V. et al. Vorinostat differentially alters 3D nuclear structure of cancer and non-cancerous esophageal cells. Scientific Reports 2016, 6, 30593.

Li, J. "Self-assembled supramolecular hydrogels based on polymer-cyclodextrin inclusion complexes for drug delivery." NPG Asia Materials 2.3 (2010): 112-118.

Park, J. et al., "Rheological behavior of hydrophilic silica dispersion in polyethylene glycol", Journal of Applied Polymer Science, Nov. 2006, vol. 103, No. 4, pp. 2481-2486 DOI:10.1002/app.23774.

Pek, Y. et al., "A thixotropic nanocomposite gel for three-dimensional cell culture", Nature Nanotechnology, Nov. 2008 [available online Sep. 2008], vol. 3, pp. 671-675 DOI:10.1038/nnano.2008.270.

Prakash, S. et al., "Strategy for Cell Therapy: Polymers for Live Cell Encapsulation and Delivery", Trends in Biomaterials and Artificial Organs, Jul. 2004, vol. 18, No. 1, pp. 24-35.

Snyder, M. et al., "Benign, 3D encapsulation of sensitive mammalian cells in porous silica gels formed by Lys-Sil nanoparticle assembly", Microporous and Mesoporous Materials, Feb. 2009 [available online Sep. 2008], vol. 118, No. 1-3, pp. 387-395 DOI:10.1016/j.micromeso.2008.09.013.

U.S. Appl. No. 61/666,602, filed Jun. 29, 2012.

Wu, Q. et al., "Rheological behavior of fumed silica suspension in polyethylene glycol", Journal of Central South University of Technology, Feb. 2006, vol. 13, No. 1, pp. 1-5 DOI:10.1007/s11771-006-0096-3.

* cited by examiner

FIG. 5A
FIG. 5B
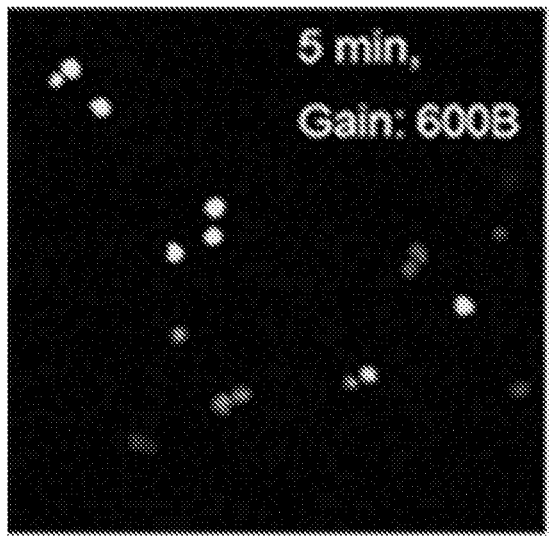
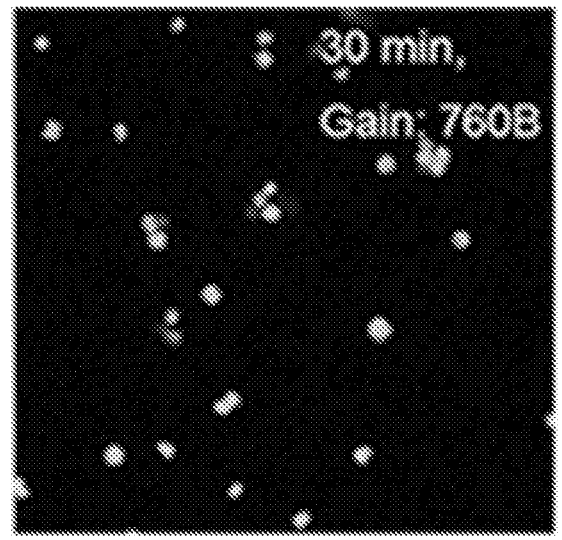
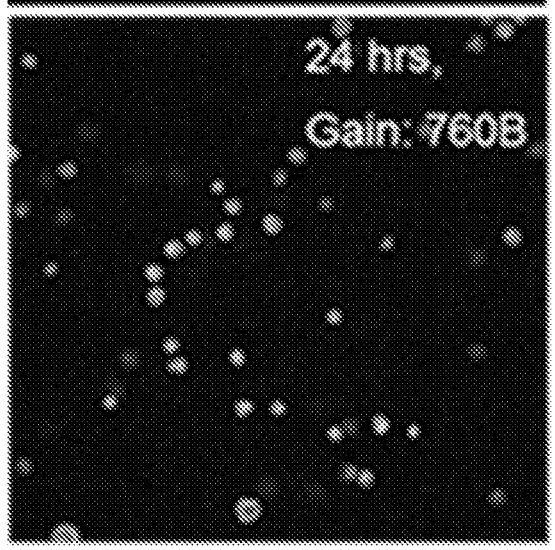
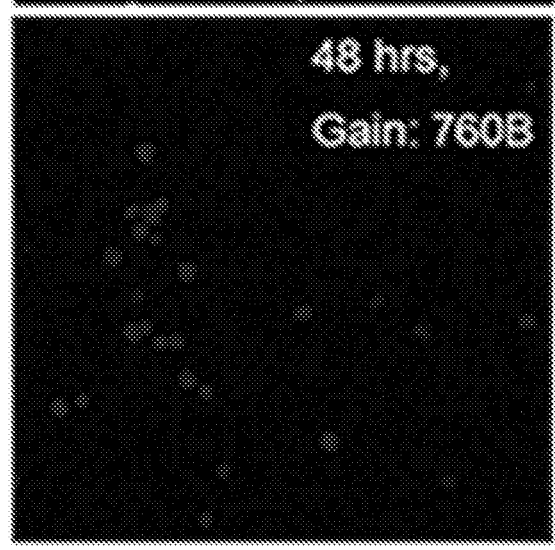
FIG. 5C
FIG. 5D

FIG. 8A
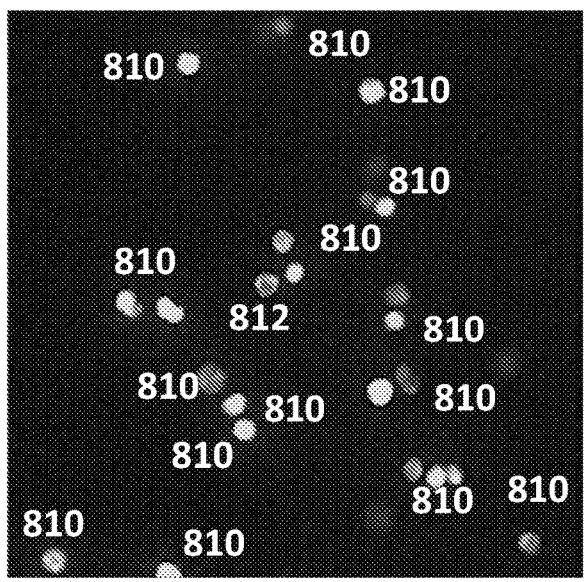
FIG. 8B
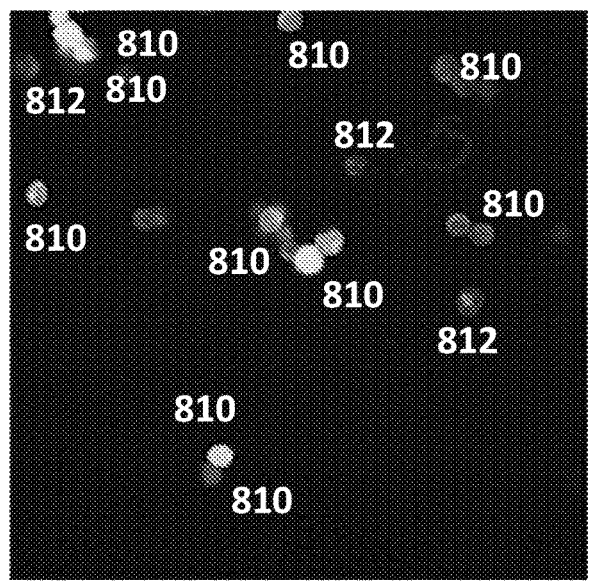
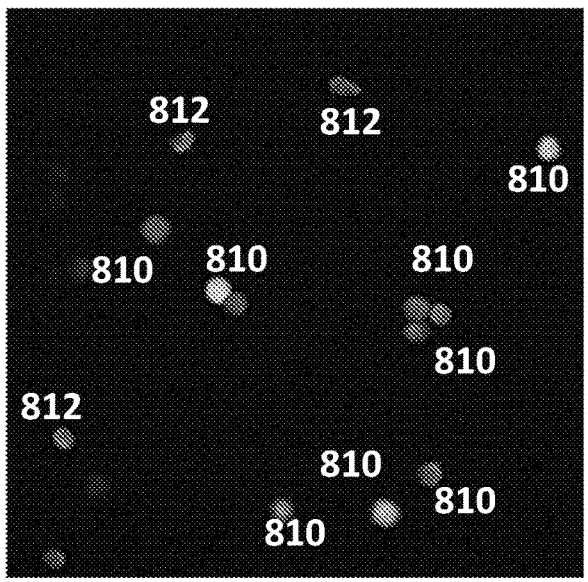
FIG. 8C
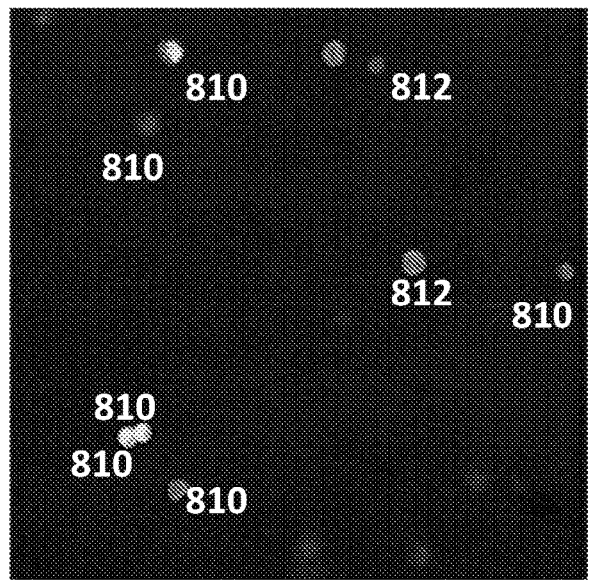
FIG. 8C

THIXOTROPIC BIOCOMPATIBLE GEL FOR LIVE CELL OBSERVATION IN CELL COMPUTED TOMOGRAPHY

CROSS REFERENCE TO RELATED APPLICATIONS

The present application is a U.S. National Stage of PCT Application No. PCT/US2018/048587 filed on Aug. 29, 2018, which claims priority from and benefit of U.S. Provisional Patent Application No. 62/553,622, filed on Sep. 1, 2017, the disclosure of which is incorporated by reference herein.

STATEMENT REGARDING FEDERALLY SPONSORED RESEARCH OR DEVELOPMENT

This invention was made with government support under P50 HG002360 awarded by the National Institutes of Health. The government has certain rights in the invention.

TECHNICAL FIELD

The present invention relates generally to biocompatible gels and, in particular, to such gels that are thixotropic and configured to maintain live cell viability and mobility in a manner that is advantageous for imaging of the cells with the use of computed tomography.

BACKGROUND

Optical computed tomography (CT) is widely used to produce quantitative 3D images of cells with isotropic spatial resolution and provide insights into and answers to biomedical questions focused on cellular architecture and function. For successful tomographic imaging, multiple 2D projections of the object (cell) can be acquired from a number of perspectives over 360 degrees. Such specific imaging has been accomplished by embedding cells in an optically transparent gel and placing them into a round glass capillary, which can be rotated with respect to the objective lens of the imaging system. This approach requires that, first, the index of refraction of the gel matches the refractive index of the capillary glass to avoid spherical aberration that would lead to substantially distorted images; and that the gel be thixotropic, i.e. characterized by viscosity that varies as a function of pressure, thereby changing from liquid (under high pressure) to solid (under substantially no pressure). This liquefaction transition is necessary to keep the cells stationary during the rotation (elastic phase) and to move the cells in the capillary (viscous phase) in and out of the field of view (FOV) of the optical lens easily, so that multiple cells can be optically interrogated. So far, the use of the optical Cell-CT has been limited to imaging fixed cells, since the commercially available gels are highly cytotoxic. As a result, the problem with the current state-of-the-art using fixed cells is that only 3D imaging snapshots of cellular architecture can be studied using the optical Cell-CT approach, whereas functional studies of cellular dynamics in live cells are still not possible.

SUMMARY

Embodiments of the disclosure describe a polymer gel comprising a polyethylene glycol (PEG) and a thickening agent. In some embodiments, the PEG is a linear PEG with an average molecular weight of about 400 g/mol. In other embodiments, the PEG is a 4-arm PEG with an average molecular weight of about 2,000 g/mol. The thickening agent is selected from the group including fumed silica, α-cyclodextrin, peptides, and polysaccharides.

Further, a method for acquiring a tomographic image of a live single cell, a plurality of live single cells, and a small amount of tissue sample is disclosed. The method contains the steps of embedding a sample in a compound polymer gel, injecting the compound polymer gel containing the sample into a capillary of an imaging cartridge of a computed tomography (CT) instrument, acquiring a plurality of 2D images of the sample embedded in the compound polymer gel during a complete rotation of the capillary, and reconstructing the plurality of 2D images into a 3D image.

BRIEF DESCRIPTION OF THE DRAWINGS

The following disclosure will be better understood from a reading of the following detailed description taken in conjunction with the drawings, in which like reference designators are used to designate like elements, and in which:

FIG. 4A is a fluorescence image of live cells in gel; FIG. 4B shows an overlay of the image of FIG. 4A with a bright field (transmission) image); FIG. 4C illustrates a fluorescence image of fixed cells in gel.

FIGS. 5A, 5B, 5C, and 5D illustrate empirically-confirmed long-term cell viability by showing changes in fluorescence signal in CPA cells (indicated with bright areas or dots) over the 48 hour period of incubation in the 15FS-20% wt/wt Keratinocyte gel. (Times at which the images were taken are indicated in the Figures). The cell viability is shown to be decreasing with time: cells remained highly viable after 24 hours (FIG. 5C), with a substantially complete loss of fluorescence signal after 48 hours of incubation indicating pronounced cell death (FIG. 5D)

FIG. 6A: a single CPA cell (approximately 10 μm in size); FIG. 6B: a cluster of three CPA cells (about 20 micron in size);

FIGS. 8A, 8B, 8C, and 8D illustrate the experimentally-verified long-term cell viability in the α-cyclodextrin-PEG20K-Keratinocyte compound gel. Shown are changes in fluorescence signal in CPA cells over 24 hours of incubation in the α-cyclodextrin-PEG20K-Keratinocyte compound gel. Cells were stained with calcein AM (green color for live cells, 810) and ethidium homodimer-1 (red color for dead cells, 820) after being mixed (FIG. 8A), and incubated for 1 hour (FIG. 8B), 2 hours (FIG. 8C) and 24 hours (FIG. 8D).

Figure 1:
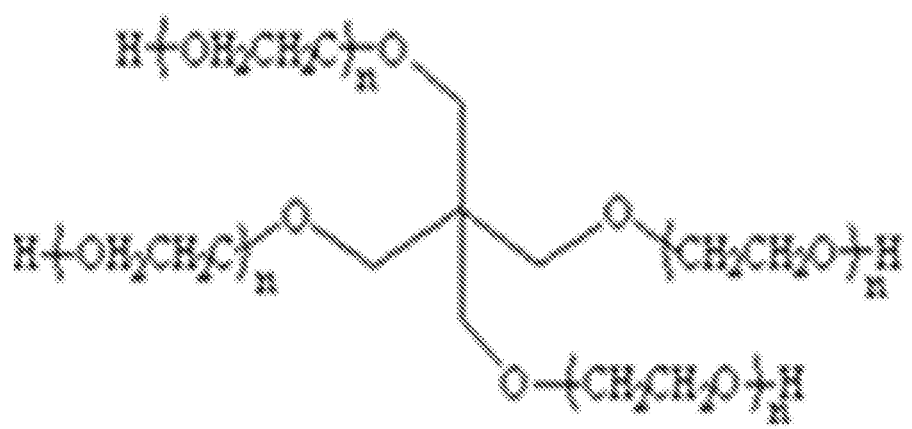
FIG. 1A illustrates a molecular structure of 4-arm polyethylene glycol (PEG).
FIG. 1B illustrates a mix of fumed silica (FS) (shown in white) with PEG (shown in black).
FIG. 1C illustrates a network of optimum dispersion of fumed silica in PEG.

The sizes and relative scales of elements in Drawings may be set to be different from actual size and scales to appropriately facilitate simplicity, clarity, and understanding of the Drawings. For the same reason, not all elements present in one Drawing may necessarily be shown and/or labeled in another.

DETAILED DESCRIPTION

Embodiments of the invention address a so-far unsolved by the related art problem of practically-implementing the imaging of a live single cell, two or more cells in a cell cluster, and/or small tissue samples with the use of optical CT. A term "single cell" refers to and is defined in reference to a stand-alone, individual cell that is not in physical contact with another cell. In this instance, the stated problem was addressed by devising a biocompatible gel that meets not only the requirements imposed by the CT-based imaging modality—and, specifically, the requirement of thixotropicity—but also possesses the refractive index that is matched closely to that of glass.

The terms "small tissue sample", "small amount of tissue sample" and similar terms refer to and define a tissue sample dimensioned to fit inside an approximately 50 um micron inside diameter) capillary, and represents a tissue sample volume of about 20 to 50 cubic microns.

Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the disclosed technology may be practiced without one or more of the specific details, or with other methods, components, materials, and so forth. In other instances, well-known structures, materials, or operations are not shown or described in detail to avoid obscuring aspects of the technology disclosed herein.

To address the creation of the medium appropriate for maintaining the live cells for CT-based imaging, specific biocompatible gels were formed at least in part as a result of combination of multi-arm polyethylene glycol with fumed silica (PEG-silica). Thixotropicity (or the level or degree of thixotropicity) of the gels with different PEG-to-silica ratios was studied with the use of a rheometer. (As is known in the art, rheological measurements are normally performed in kinematic instruments in order to get quantitative results to determine the viscoelastic properties (such as gel strength and yield value, for example). A rheometric measurement normally includes a strain (deformation) or a stress analysis at a chosen constant frequency optionally combined with a frequency analysis (e.g. between 0.1 and 100 Hz). The strain sweep gives information of the elastic modulus G', the viscous modulus G" and the phase angle S. A large value of G' in comparison to G" indicates pronounced elastic properties of the product being analyzed (gel in this case). A phase angle of 0° implies a perfectly elastic material, while a phase angle of 90° means a perfectly viscous material. The optional frequency sweep provides information about the gel strength: here, a large slope of the G' curve indicates low strength and a small slope value indicates high strength of the material in question.) As used herein, thixotropicity is defined as a property of a material to become less viscous under stress and return to its original state when stress is removed. It was empirically found that a degree of thixotropicity was affected by the ratio of PEG to silica. In certain embodiments, thixotropicity was assessed by comparing phase angles representing the material before and after liquefaction transition, respectively. For a fully thixotropic material, these two phase angles are substantially the same.

Further, biocompatibility of the implemented gels was determined using fluorescence viability assays of metastatic esophageal epithelial and cervical adenocarcinoma cells, particular with the use of fluorescence microscopy. As used herein, the gel is considered to be biocompatible when the live cells stay alive in or in contact with the gel and the gel are not harmful to (does not substantially alter the viability of) the live cells. The cell suspension in PBS or culture medium was intermixed with the PEG-silica gel to uniformly disperse the cells in the gel, and the mixture was then placed in an incubator before adding the fluorescence dyes for live-dead assays. Calcein AM was used as a label for live cells. It was empirically determined that the cells remained viable (live) in the gels for different durations—from a short amount of time to the time on the order of one day—depending on the composition of a particular gel. In some embodiments, the cells in the gel comprising 15FS-5% Keratinocyte had a viability up to 2 hours. In other embodiments, the cells in the gel containing 15FS-10% Keratinocyte remained viable up to 6 hours. In yet other embodiments, the cells in the gel comprising 15FS-30% Keratinocyte remained viable up to 24 hours. It was empirically proven, therefore, that the so-formed gels are suitable for the live cell imaging in general, and can be utilized for live cell optical computed tomography, in particular.

With respect to the compositions of the gel, in certain embodiments a polymer gel includes a linear polyethylene glycol (PEG) with an average molecular weight of about 400 g/mol and a thickening agent. In certain embodiments, a polymer gel including a 4-arm PEG (having a structure depicted below as Structure 1)

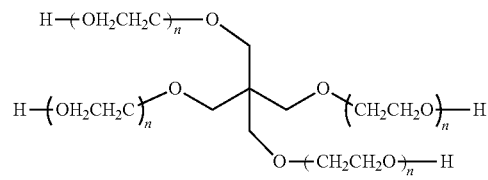

Structure 1 and a thickening agent. PEG with different molecular weight can be utilized here. In some embodiments, 4-arm PEG with a molecular weight range of about 1,500 g/mol to about 2,500 g/mol was used. In related embodiments, 4-arm PEG with an average molecular weight of 2,000 g/mol was used. In yet other embodiments, PEG with a molecular weight of 10,000 g/mol was used. In further embodiments, PEG with a molecular weight of 20,000 g/mol was used. In still other embodiments, PEG with a molecular weight of 35,000 g/mol was used to achieve the desired result Further, different thickening agents were used in different implementations: in some embodiments, fumed silica was employed as the thickening agent, while in other embodiments, the used thickening agent was α-cyclodextrin. Other suitable thickening agents, such as starches and proteins, can also be used, in the alternative, to form the polymer gel. Moreover, different weight percentages of fumed silica and PEG were used in different gels: in certain embodiments, the fumed silica was about 7% by weight to about 15% by weight and the PEG was about 93% by weight to about 85% by weight.

Further, a polymer gel is mixed with a judiciously-chosen medium to form a compound polymer gel. The selection of the medium was dependent on the type of cells used. In certain embodiments, such medium was selected from phosphate-buffered saline (PBS), Dulbecco's Modified Eagle Medium (DMEM), Keratinocyte medium, and any combination thereof. In some embodiments, the medium was Keratinocyte medium.

TABLE 1 different examples of compositions of a compound polymer gel.

| Samples | Composition | | | | Phase Angles (°) |
|---|---|---|---|---|---|
| | αCD (g/mL) | PEG (g/ml) | MW$_{PEG}$ | Liquid | |
| αCD-PEG20K-Water | 0.193 | 0.266 | 20,000 | DI Water | 14$^a$-90$^b$-76$^{c*}$ |
| αCD-PEG20K-PBS | 0.193 | 0.266 | 20,000 | PBS | 8-84-35 |
| αCD-PEG20K-Keratinocyte | 0.193 | 0.266 | 20,000 | Keratinocyte | 8-89-17 |
| αCD-PEG10K-Keratinocyte | 0.193 | 0.266 | 10,000 | Keratinocyte | 9-90-68 |
| αCD-PEG35K-Keratinocyte | 0.193 | 0.266 | 35,000 | Keratinocyte | 17-85-22 |

*$^a$the starting phase angle of the gel;
$^b$the phase angle after shear stress is applied;
$^c$the final phase angle after stress is removed.
45° is the interface between liquid and gel.

Information contained in Table 1 additionally demonstrates that a degree of thixotropicity of a given sample is affected by the molecular weight of PEG and the type of solution. The following description provides additional information with the use of which a skilled artisan will appreciate how to make and use the invention. The discussed examples are intended to be non-limiting and incorporate appropriate modifications and changes.

Figure 1B:
Figure 1C:
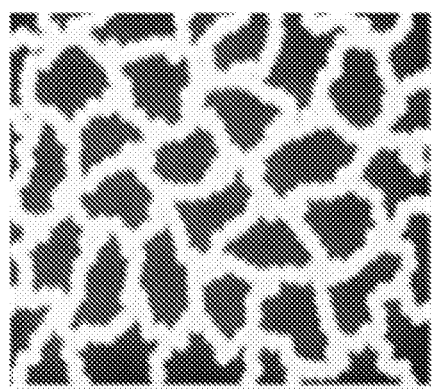

Development of Thixotropic Biocompatible Gels for Live Cell Observation in Cell-CT The components of base gels. The thixotropic and biocompatible gels were developed by combining 4-arm polyethylene glycol (PEG) with fumed silica (the combination that is herein referred to as PEG-silica). PEG with a molecular weight of 2,000 g/mol (FIG. 1A) was selected as a base material due to its biological compatibility and optical properties. Fumed silica was used as a thickening agent to adjust the thixotropic properties of the gels (FIGS. 1A and 1B).

Figure 2:
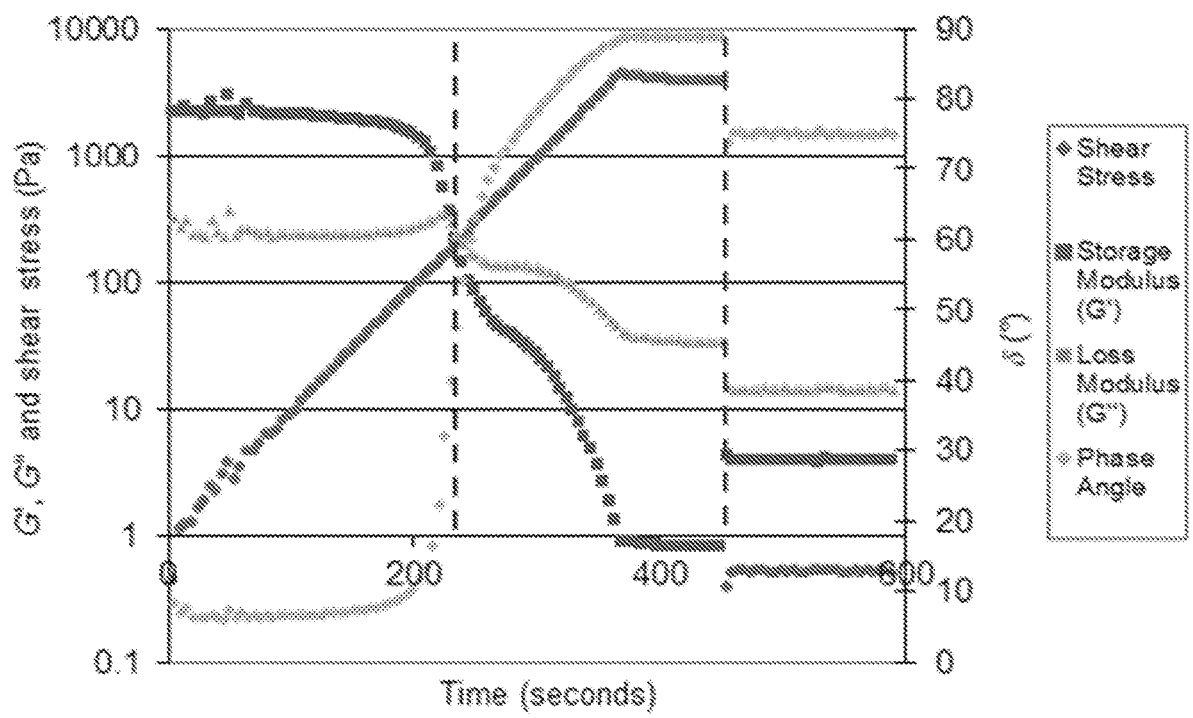
FIG. 2 includes plots representing viscoelastic properties of a gel containing 8% fumed silica as a function of increasing shear stress ti applied over time. At the time of 235 s, when shear storage modulus equals the shear loss module, liquefaction (transition from a solid (elastic phase) to a fluid (viscous phase)) occurs.

The rheological properties of gels. The thixotropic properties of the PEG-silica gels were characterized with a rheometer to measure the storage modulus, loss modulus, and phase angle as a function of shear stress on the gels. FIG. 2 shows results of a typical measurement of viscoelastic properties of a polymer gel containing 8% fumed silica. With the increase of shear, the gel became less viscous, with liquefaction occurring when a shear force of 180 Pa was reached at about 235 seconds, causing the gel to transition into a liquid, less viscous state. After stress was removed, the gel reversed to a more viscous form (while not necessarily completely returning to the solid state, as evidenced by a final phase angle of 75 degrees).

To investigate how the viscoelastic properties of the gels change as a function of the amount of fumed silica, a series of gels containing between 5 and 15% fumed silica (in 1% increments) was procured. Rheological measurements of this series of gels demonstrated that the ratio of fumed silica to PEG markedly affected thixotropicity of the gels. In particular, no liquefaction was observed in gels containing 5%, 6%, and 7% of fumed silica, with these gels behaving essentially as viscous liquids. However, the liquefaction was observed in gels containing at least 8% of fumed silica. A further increase of fumed silica content in a gel resulted in higher viscosity, higher level of stress required for liquefaction to occur, and reduction in final values of phase angles after stress removal, which is evidence of increased degree of thixotropicity. A gel formulation containing 15% of fumed silica showed liquefaction at the stress level of 1,700 Pa with a final phase angle of 38 degrees. Due to the liquefaction and return to the viscous phase after stress removal, this specific gel formulation (abbreviated as 15FS) was used in the following biocompatibility study.

Gel Systems Formed by Mixing 15FS Gel with Various Liquids at Different Ratios.

In the following, different concentrations of the Keratinocyte medium were used to address two different questions: first, the maximum amount of the medium that still maintains thixotropic property of the gel, and, second, cell viability in the gel.

Figure 3:
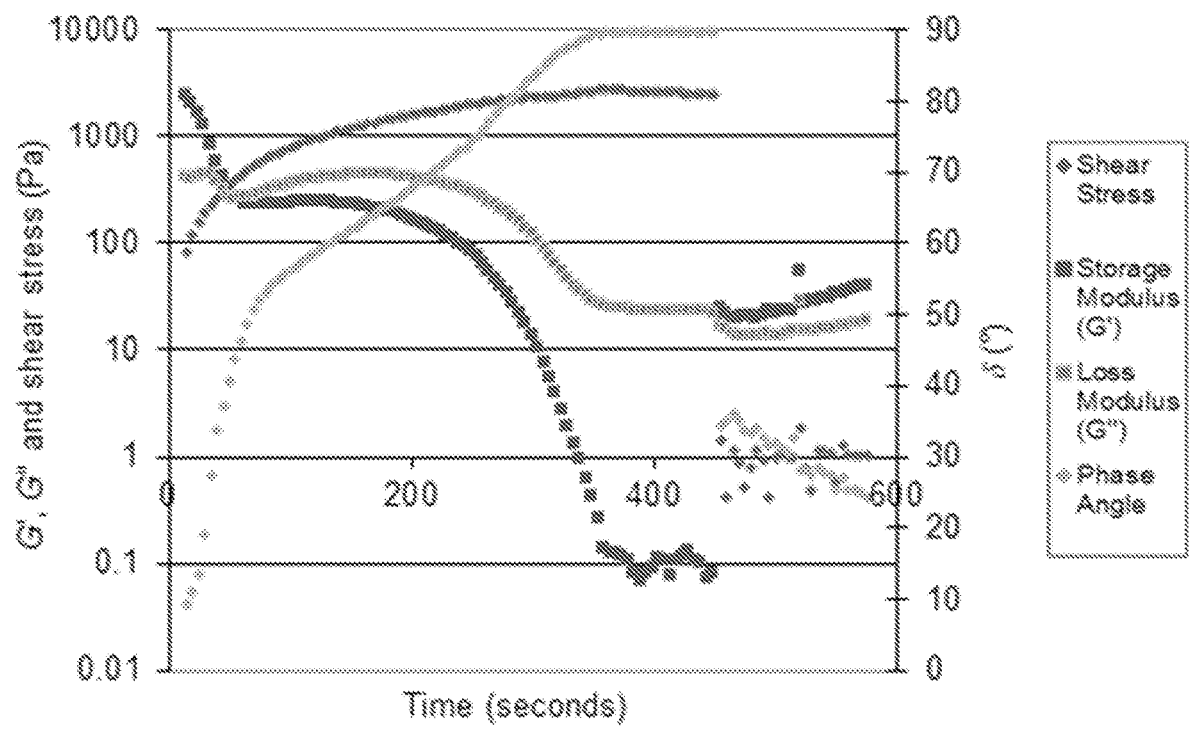
FIG. 3 includes plots representing results of a measurement of viscoelastic properties of the 15FS gel containing 30% wt/wt Keratinocyte medium. Liquefaction occurs at 56 s and a shear stress of 390 Pa. The thixotropicity of the sample is demonstrated by the change of the value of phase angle from about 5 degrees to about 90 degrees after liquefaction, and back to about 15 degrees after the stress is removed.
Figure 4A:
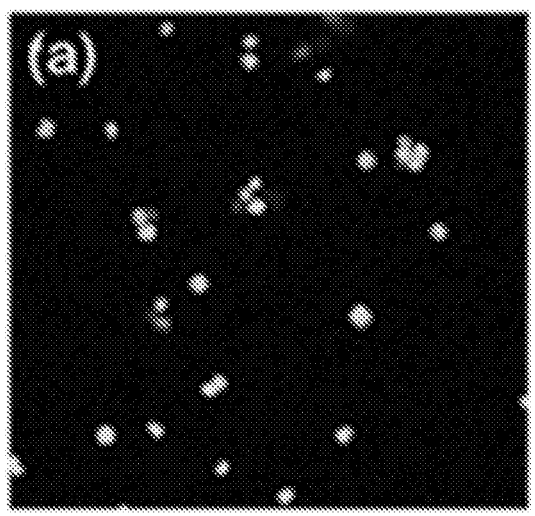
FIGS. 4A, 4B, 4C, and 4B illustrate results of a biocompatibility test with the use of human metaplastic esophageal epithelial cells (CPA cell line) in the compound 15FS gel containing 20% wt/wt of Keratinocyte medium.
Figure 4B:
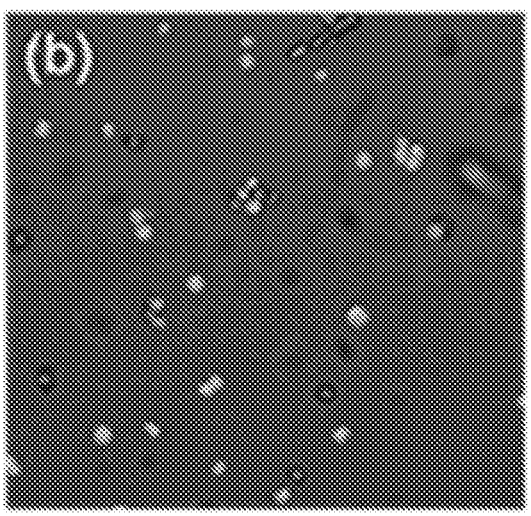
Figure 4C:
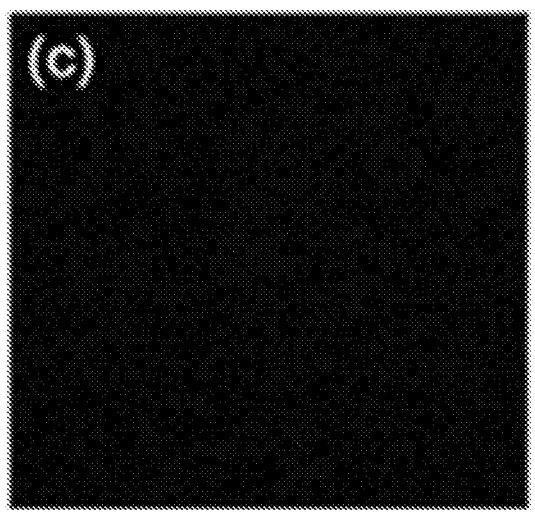
Figure 4D:
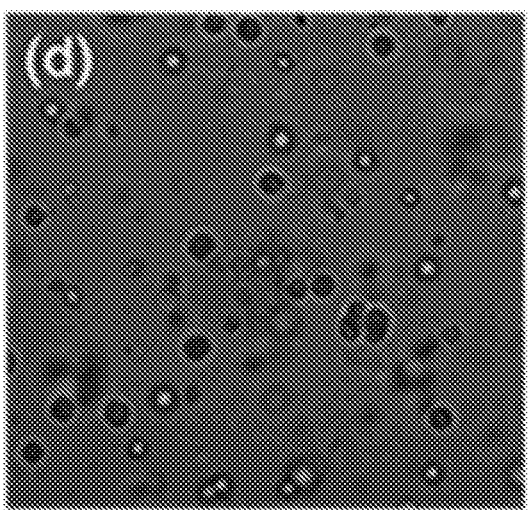
FIG. 4D presents an overlay of the image of FIG. 4C with a transmission image.

To increase a degree of biocompatibility of a gel formulation, the 15FS gel was mixed with varying amounts of PBS and cell culture media to form compound gels. The viscoelastic properties of the compound gels were then characterized using the rheometer (Table 2). First, the 15FS gel was mixed with four types of liquid: water, PBS, Dulbecco's Modified Eagle Medium (DMEM) or Keratinocyte medium at a ratio of 800 µg of 15FS to 200 µL of medium. It was observed that, while the addition of water to the gel resulted in a complete loss of thixotropicity, the addition of PBS and the DMEM and Keratinocyte media did not (FIG. 3).

TABLE 2

Viscoelastic properties of different gel formulations

| Samples | FS fraction (wt %) | PEG fraction (wt %) | Medium loading (vol %) | Phase Angles (°) |
|---|---|---|---|---|
| 7FS | 7 | 93 | 0 | 72-89-80 1 |
| 8FS | 8 | 92 | 0 | 30-89-75 |
| 9FS | 9 | 91 | 0 | 26-89-70 |
| 10FS | 10 | 90 | 0 | 28-89-67 |
| 11FS | 11 | 89 | 0 | 21-86-63 |

TABLE 2-continued

Viscoelastic properties of different gel formulations

| Samples | FS fraction (wt %) | PEG fraction (wt %) | Medium loading (vol %) | Phase Angles (°) |
|---|---|---|---|---|
| 12FS | 12 | 88 | 0 | 19-80-56 |
| 13FS | 13 | 87 | 0 | 24-78-51 |
| 14FS | 14 | 86 | 0 | 24-69-45 |
| 15FS | 15 | 85 | 0 | 20-63-38 |
| 15FS-20% Water | 12 | 68 | 20 | 51-89-53 |
| 15FS-20% PBS | 12 | 68 | 20 | 8-88-31 |
| 15FS-20% DMEM | 12 | 68 | 20 | 8-81-12 |
| 15FS-30% DMEM | 10.5 | 59.5 | 30 | 8-90-25 |
| 15FS-20% Keratin | 12 | 68 | 20 | 6-82-18 |
| 15FS-30% Keratin | 10.5 | 59.5 | 30 | 7-90-25 |

[1]72-89-80, 72 is the starting angle, 89 is the liquefaction angle, and 80 is the angle after shear stress is removed. For highly thixotropic materials, the low starting shear angle should increase to ~90 degrees when liquefaction occurs followed by a return to the same value after the stress is removed.

After establishing which gel formulations exhibit strong thixotropic properties, the biocompatibility of the gels was further examined using a fluorescence viability assay and fluorescence imaging. Calcein AM was used for labeling live cells. The results indicated that cells remained viable for a period of time from a few tens of minutes up to one day in the gels depending on the composition. (Since the addition of medium to the 15FS gel will decrease the thixotropic property, it was shown, via the rheology test, that thixotropicity could be kept even up to 30% of Keratinocyte medium was added.)

Referring to FIGS. 4A, 4B, 4C, and 4D, shown are two sets of cells mixed with the 15FS polymer gel containing 20% Keratinocyte medium by weight. At about 30 minutes after incubation the cells showed strong fluorescence of Calcein AM indicating viable cells, while under same imaging conditions, the fixed cells did not show any fluorescence. (The cells have viability in the gel with small amount of medium, such as 20%)

Referring to FIGS. 5A. 5B, 5C, and 5D, the long-term viability of cells in gels were characterized. Changes in fluorescence signal of CPA cells over incubation time in the 15FS compound gel containing 20% w/w of Keratinocyte cell culture medium were recorded. Cells remained highly viable after 24 hours, with a complete loss of fluorescence after 48 hour incubation period, thereby indicating cell death. Accordingly, in one embodiment the compound polymer gel is configured to sustain a live cell up to about 48 hours.

Figure 6A:
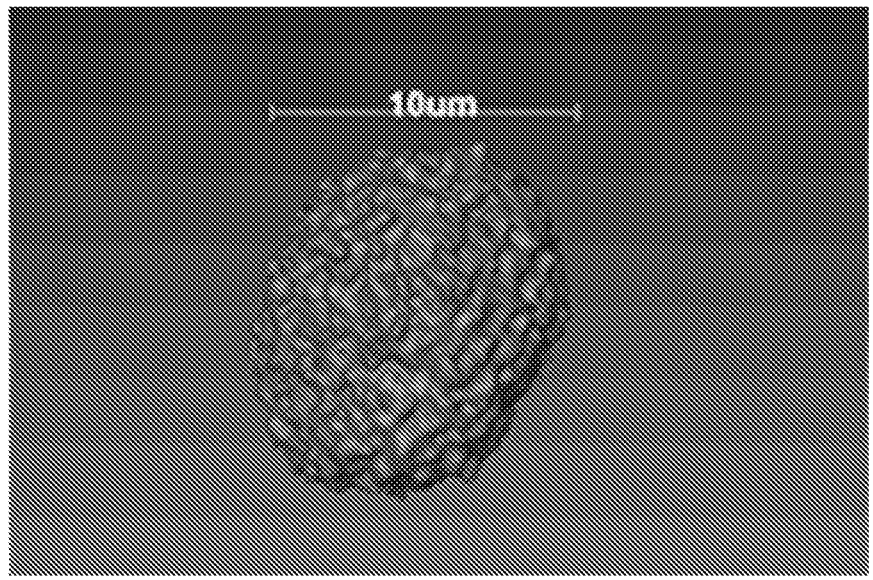
FIGS. 6A and 6B contain CT images of CPA cells contained in 15FS-20% wt/wt Keratinocyte for 30 minutes and then stained with Calcein AM.
Figure 6B:
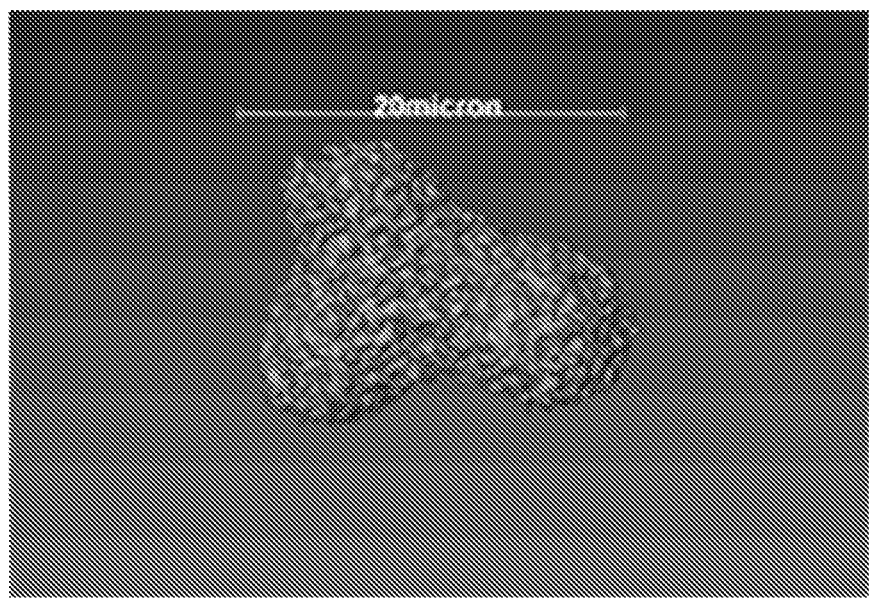

To demonstrate the utility of the gel for performing live Cell-CT, the Cell-CT setup (discussed by Nandakumar, V. et al. in "Isotropic 3D nuclear morphometry of normal, fibrocystic and malignant breast epithelial cells reveals new structural alterations"; PLoS One 2012, 7, e0029230, doi: 10.1371/journal.pone.0029230, contents of which are incorporated by reference herein) was used to collect 2D projections (images) of cells stained with Calcein AM, followed by 3D reconstruction of the image data. FIGS. 6A, 6B show 3D isosurface volumetric renderings of a single cell (FIG. 6A) and a cluster of 3 cells (FIG. 6B) These data demonstrate that the used gel formulation was configured to and was able to not only maintain viable, live cells, but was also compatible with and was facilitating high resolution imaging in 3D performed with the use of the computed tomography methodology.

Figure 7:
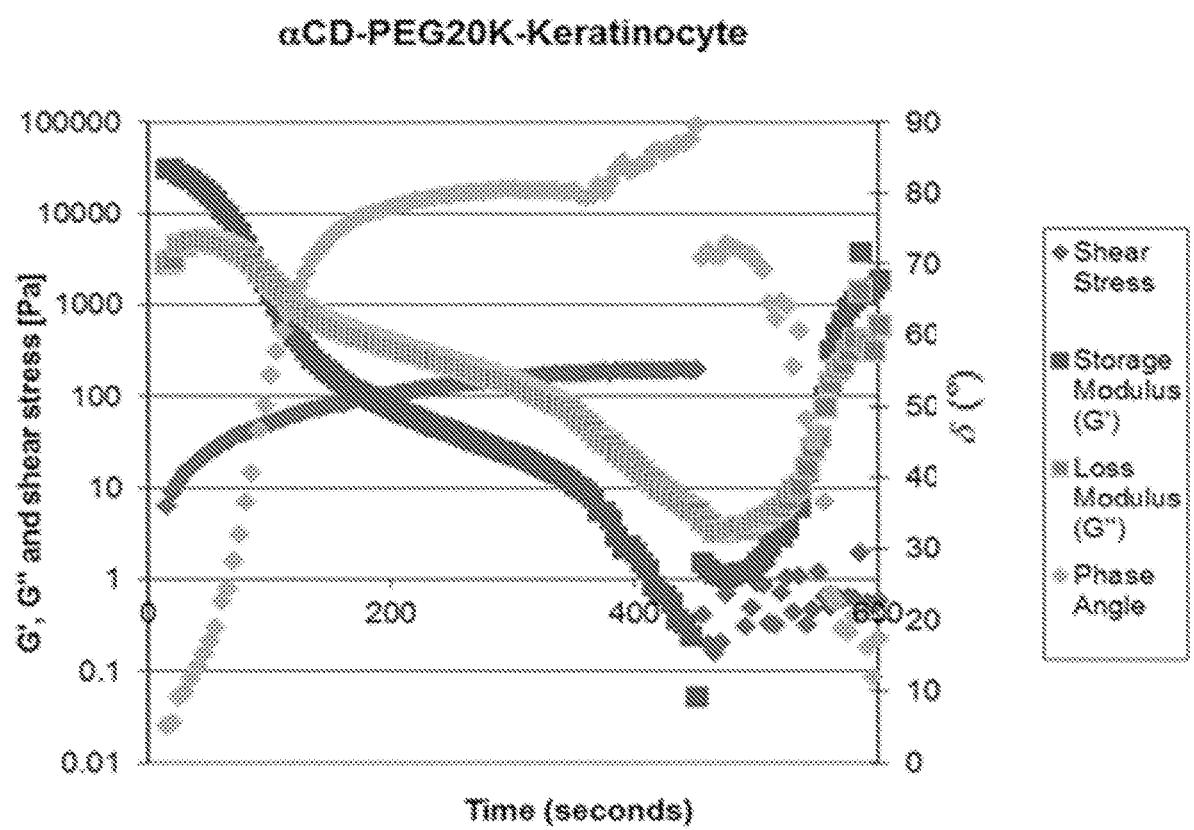
FIG. 7 displays the plots representing results of a typical measurement of viscoelastic properties of the α-cyclodextrin-PEG20K-Keratinocyte compound gel; the observed change (increase) of the phase angle from about 8 degrees to about 89 degrees and the following decrease to about 17 degrees indicates and evidences that this particular implementation of gel possess practically desired thixotropicity.

Besides polyethylene glycol, α-cyclodextrin was also used as the thickening agent in this study. FIG. 7 illustrates the rheological properties of α-cyclodextrin (CD)-PEG20K-Keratinocyte (listed in Table 1; 0.193 g α-CD and 0.266 g PEG with a molecular weight of 20000 were added to 1 gram of Keratinocyte) compound gel. As a person of skill I the art will readily recognize from the plots of FIG. 7, this implementation of the gel has a very good and practically appropriate (for the purposes of the chosen imaging methodology) thixotropic property. For example, the phase angle values measured before and after the occurrence of liquefaction are substantially equal, indicating that the material returned to its viscous (elastic) state after having the applied pressure removed.

Referring now to FIGS. 8A, 8B, 8C, and 8D, the viability test of 5% CPA cells in 95% α-cyclodextrin-PEG20K-Keratinocyte compound gel was carried out. Specifically, calcein AM was added after the incubation of the mixture at time 0, 1 hr, 2 hrs and 24 hrs. With a 10 minute delay after addition of Calcein AM, ethidium homodimer-1 was added, and the incubation continued for 10 more minutes. The in situ observation with the use of confocal microscope indicates that this gel had very good biocompatibility (in terms of cells being viable after being embedded in gel for prolonged periods of time).

It is appreciated, therefore, that biocompatible thixotropic gels were formulated by combining 4-arm polyethylene glycol with fumed silica. The rheology measurements indicated that thixotropicity of the gels increased with an increasing ratio of PEG to fumed silica. A compound gel containing 15% fumed silica and 20% Keratinocyte cell culture medium was found to be the most biocompatible formulation with robust thixotropic properties capable of sustaining cell viability for up to one day. As a result, the 15FS-20% Keratinocyte medium formulation as proven to be suitable for long-term live cell imaging and compatible with the live cell CT imaging modality.

Accordingly, the scope of the invention covers a methodology for acquiring a tomographic image of a live single cell. Such method includes the step of embedding the live single cell in a compound polymer gel that contains i) a 4-arm polyethylene glycol (PEG) that has a structure represented by Structure 1 (discussed above) and ii) a thickening agent. The methodology further includes injecting the compound polymer gel containing such cell into a capillary of an imaging cartridge of a computed tomography (CT) instrument; acquiring a plurality of 2D images of such cell embedded in the compound polymer gel during a complete rotation of the capillary; and reconstructing the plurality of 2D images into a 3D image. (A complete rotation of the cell—typically, over the range of 360 degrees—is required to produce a full dataset of 2D projection images, which are then used to reconstruct a volumetric 3D image of the object. In case of incomplete rotation, the results of the 3D reconstruction will typically have artifacts and reduced spatial resolution and contrast.)

Further, the step of embedding may include dispersing a plurality of live single cells is the compound polymer gel. Alternatively or in addition, the step of embedding may include dispersing a small amount of tissue sample in the compound polymer gel.

Materials and Methods.

4-arm polyethylene glycol (PEG) was obtained from JenKem Technology USA Inc., fumed silica was from Sigma-Aldrich, Calcein AM is from Life Technologies.

Preparation of Gel. The stock solution of 4-arm polyethylene glycol (PEG) was filtered through a 0.45 μm syringe filter. Fumed silica (FS) (Cab-o-sil M5, sigma) was added to 4-arm PEG at a weight ratio ranging from 5% to 15% and stirred until a homogeneous mixture was formed. For example, a gel with 5% FS was formed by adding 0.05 g of FS into 0.95 g of PEG and magnetically stirred for an hour.

Cell culture and redispersion in PBS. CPA cells were cultured in Keratinocyte serum-free medium (Invitrogen, Carlsbad, CA) supplemented with Bovine Pituitary Extract (BPE) and human recombinant Epidermal Growth Factor (rEGF, Invitrogen), 100 unit/ml penicillin at 37° C. in a 5% $CO_2$ atmosphere. When a confluence reached 80%, the medium was aspirated, and the cells were washed with PBS and trypsinized. The trypsinization was blocked by adding Dulbecco's Modified Eagle Medium (DMEM) to the suspension. The cells were spun down and re-suspended in PBS or medium afterwards.

Preparation of sample for Cell-CT (cell+gel). To uniformly disperse cells in gels, the PBS cell suspension (1% to 10% by volume) was added to the gel by gentle trituration. Further steps of introduction of the prepared gel for imaging with optical Cell-CT are described in Nandakumar, V. et al. The gel containing cells was then introduced into a syringe and injected into a round capillary of the imaging cartridge of the CT instrument (Cell-CT, VisionGate Inc., Gig Harbor, WA). Five hundred 2D projections (images) of live cells embedded in the gel were taken during a full rotation of the capillary followed by 3D reconstruction of volumetric images using a simultaneous iterative reconstruction algorithm. A person of ordinary skill in the art would recognize and appreciate the use of methods known in the art to complete a 3D reconstruction of volumetric image.

Cell Viability Tests. For viability tests, the mixture of gel and cells was placed in an incubator at 37° C. for desired amounts of time. 1 µL of Calcein AM (Molecular Probes) was added to 49 µL of the mixture of gel and cells resulting in a final concentration of the dye of 2.5 µM. After incubating for 30 minutes, the sample was spread on a cover glass for confocal observation.

Confocal Optical Imaging. A confocal microscope (C1Si, Nikon, Melville, NY) was used for fluorescence imaging of live cells stained with Calcein AM. Fluorescence of the dye was excited at 488 nm and detected with in a spectral range of 515±15 nm. As Calcein AM becomes fluorescent only as a result of enzymatic activity of esterases in live cells, live cells show strong green fluorescence signal in micrographs, whereas dead cells are non-fluorescent.

Rheology Measurements. The viscoelastic measurements were performed using an automated, computer controlled rheometer (PP25-S, Anton Parr, Ashland, Virginia) that enabled varying shear stress to be applied over a period of time. The data output consisted of the shear storage modulus, loss modulus and phase angle.

If and when, for the purposes of this disclosure and the appended claims, the use of the terms "substantially", "approximately", "about" and similar terms is made in reference to a descriptor of a value, element, property or characteristic at hand, such term is intended to emphasize that the value, element, property, or characteristic referred to, while not necessarily being exactly as stated, would nevertheless be considered, for practical purposes, as stated by a person of skill in the art. Such term(s) terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 10% with respect to the specified value, more preferably plus or minus 5%, most preferably plus or minus 2% with respect to the specified value. As a non-limiting example, two values being "substantially equal" to one another implies that the difference between the two values may be within the range of +/−10% range of the value itself, more preferably within the range of +/−5% of the value itself, and even more preferably within the range of +/−2% or less of the value itself.

The use of such term(s) in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

An embodiment of the system configured to implement or characterize an embodiment of the invention may include electronic circuitry (for example, a computer processor) controlled by instructions stored in a memory, to perform specific data collection/processing and calculation steps as disclosed above. The memory may be random access memory (RAM), read-only memory (ROM), flash memory or any other memory, or combination thereof, suitable for storing control software or other instructions and data. Those skilled in the art should would readily appreciate that instructions or programs defining the operation of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement a method of the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

The invention as recited in claims appended to this disclosure is intended to be assessed in light of the disclosure as a whole. Disclosed aspects, or portions of these aspects, may be combined in ways not listed above. Accordingly, the invention should not be viewed as being limited to the disclosed embodiment(s).

It should be appreciated by a person skilled in the art that modifications and adaptations to those embodiments may occur without departing from the scope of the invention.

What is claimed is:

1. A compound polymer gel comprising:
a polymer gel mixed with a Keratinocyte medium, wherein the polymer gel comprises:
(i) a polyethylene glycol that is selected from the group consisting of:
a 4-arm polyethylene glycol (4-arm PEG) having a structure of

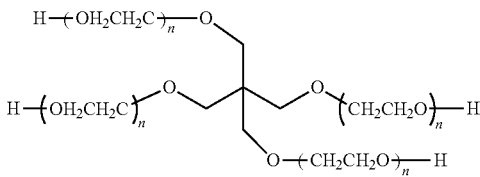

and a linear PEG,
wherein a value of n is defined such that, when the 4-arm PEG is selected, an average molecular weight of the polyethylene glycol ranges from about 1,500 to about 35,000 g/mol;

(ii) a thickening agent that is fumed silica;
wherein the polyethylene glycol is about 93% by weight to about 85% by weight of the polymer gel while the thickening agent is about 7% by weight to about 15% by weight of the polymer gel,
and
wherein the compound polymer gel is configured to sustain a live cell up to about 48 hours.

2. The compound polymer gel of claim 1, wherein the 4-arm PEG has an average molecular weight range of about 1,500 to about 2,500 g/mol.

3. The compound polymer gel of claim 2, wherein the 4-arm PEG has an average molecular weight of about 2,000 g/mol.

4. The compound polymer gel of claim 1, wherein the linear PEG has an average molecular weight of about 400 g/mol.

5. The polymer gel of claim 1, wherein the fumed silica is about 7% by weight of said polymer gel.

6. The polymer gel of claim 1, wherein the fumed silica is about 15% by weight of said polymer gel.

* * * * *